United States Patent
Imamura

(10) Patent No.: US 9,934,435 B2
(45) Date of Patent: Apr. 3, 2018

(54) IMAGE PROCESSING APPARATUS AND IMAGE PROCESSING METHOD

(71) Applicant: CANON KABUSHIKI KAISHA, Tokyo (JP)

(72) Inventor: Hiroshi Imamura, Kyoto (JP)

(73) Assignee: Canon Kabushiki Kaisha, Tokyo (JP)

( * ) Notice: Subject to any disclaimer, the term of this patent is extended or adjusted under 35 U.S.C. 154(b) by 318 days.

(21) Appl. No.: 14/371,752

(22) PCT Filed: Feb. 13, 2013

(86) PCT No.: PCT/JP2013/054061
§ 371 (c)(1),
(2) Date: Jul. 11, 2014

(87) PCT Pub. No.: WO2013/125545
PCT Pub. Date: Aug. 29, 2013

(65) Prior Publication Data
US 2014/0354794 A1   Dec. 4, 2014

(30) Foreign Application Priority Data

Feb. 20, 2012  (JP) .................................. 2012-034539
Nov. 7, 2012   (JP) .................................. 2012-245637

(51) Int. Cl.
*H04N 7/18*   (2006.01)
*G06K 9/00*   (2006.01)
(Continued)

(52) U.S. Cl.
CPC ............ *G06K 9/00604* (2013.01); *A61B 3/00* (2013.01); *A61B 3/1025* (2013.01);
(Continued)

(58) Field of Classification Search
CPC ......... G06T 3/4069; G06T 2207/30041; G06T 7/0012; G06T 2207/10064; G06T 3/4038; G06T 2207/30101; G01N 21/4795
(Continued)

(56) References Cited

U.S. PATENT DOCUMENTS 5,885,218 A * 3/1999 Teo .......................... A61B 8/12
                                                        600/443
6,464,641 B1 * 10/2002 Pan ........................ A61B 8/06
                                                        600/453
(Continued)

FOREIGN PATENT DOCUMENTS

JP   2007-330582 A   12/2007
JP   2011-087813 A   5/2011

OTHER PUBLICATIONS

Johnny Tam, et al., "Noninvasive Visualization and Analysis of Parafoveal Capillaries in Humans", Investigative Ophthalmology & Visual Science, vol. 51, No. 3, Mar. 2010, pp. 1691-1698.
(Continued)

*Primary Examiner* — Helen Shibru
(74) *Attorney, Agent, or Firm* — Fitzpatrick, Cella, Harper & Scinto

(57) ABSTRACT

An image processing apparatus determines an exceptional frame of a plurality of frames forming a moving image captured by an ophthalmic apparatus including an aberration correction device, and applies image processing of a blood vessel area for a frame, among the plurality of frames, which has not been determined as the exceptional frame.

6 Claims, 12 Drawing Sheets

(51) Int. Cl.
  *A61B 3/00* (2006.01)
  *G06T 7/00* (2017.01)
  *G06T 7/254* (2017.01)
  *A61B 3/10* (2006.01)
  *A61B 3/12* (2006.01)
  *A61B 5/024* (2006.01)
  *A61B 5/0285* (2006.01)

(52) U.S. Cl.
  CPC ........ *G06K 9/00127* (2013.01); *G06T 7/0012* (2013.01); *G06T 7/254* (2017.01); *A61B 3/1015* (2013.01); *A61B 3/1233* (2013.01); *A61B 5/0285* (2013.01); *A61B 5/02416* (2013.01); *G06T 2207/30041* (2013.01); *G06T 2207/30104* (2013.01)

(58) Field of Classification Search
  USPC ...... 348/78, 77, 68; 382/134, 128, 132, 203, 382/216, 217, 218, 115
  See application file for complete search history.

(56) References Cited

U.S. PATENT DOCUMENTS

| | | | |
|---|---|---|---|
| 7,530,692 | B2 | 5/2009 | Yamaguchi et al. |
| 7,537,340 | B2* | 5/2009 | Yamaguchi .............. A61B 3/14 351/205 |
| 8,504,141 | B2 | 8/2013 | Suehira et al. |
| 8,840,248 | B2 | 9/2014 | Imamura |
| 2006/0078170 | A1* | 4/2006 | Kamata .................... G06K 9/00 382/115 |
| 2007/0291230 | A1 | 12/2007 | Yamaguchi et al. |
| 2008/0137934 | A1* | 6/2008 | Sakaguchi ........... A61B 6/4441 382/132 |
| 2008/0221439 | A1* | 9/2008 | Iddan ................... A61B 6/5217 600/424 |
| 2008/0294038 | A1* | 11/2008 | Weese ................... A61B 6/481 600/431 |
| 2010/0149073 | A1* | 6/2010 | Chaum .............. G02B 27/0093 345/8 |
| 2010/0183116 | A1* | 7/2010 | Zaiki ...................... A61B 6/464 378/8 |
| 2010/0195048 | A1 | 8/2010 | Hammer et al. |
| 2011/0037845 | A1* | 2/2011 | Mensink ................ G06T 3/4069 348/78 |
| 2011/0096996 | A1* | 4/2011 | Mohamed ............... G06T 19/20 382/203 |
| 2011/0098560 | A1 | 4/2011 | Suehira et al. |
| 2011/0137157 | A1 | 6/2011 | Imamura et al. |
| 2012/0063660 | A1 | 3/2012 | Imamura et al. |
| 2012/0075449 | A1* | 3/2012 | Yasuda .............. A61B 1/00009 348/68 |
| 2012/0130270 | A1 | 5/2012 | Imamura et al. |
| 2012/0140170 | A1* | 6/2012 | Hirose ................. A61B 3/1233 351/206 |
| 2012/0154567 | A1* | 6/2012 | Yamaguchi .......... A61B 1/0638 348/68 |
| 2012/0300903 | A1* | 11/2012 | Yao .......................... A61B 6/12 378/62 |
| 2013/0058553 | A1 | 3/2013 | Yonezawa et al. |
| 2014/0085606 | A1 | 3/2014 | Miyasa et al. |
| 2014/0112566 | A1* | 4/2014 | Steinberg ............. A61B 5/0044 382/131 |
| 2014/0240667 | A1 | 8/2014 | Uji et al. |
| 2014/0240668 | A1 | 8/2014 | Uji et al. |
| 2014/0240669 | A1 | 8/2014 | Imamura |
| 2016/0015348 | A1* | 1/2016 | Ohishi ................... A61B 6/481 600/431 |
| 2016/0019691 | A1* | 1/2016 | Imamura .................. G06T 5/50 382/128 |

OTHER PUBLICATIONS

May 21, 2013 International Search Report and Written Opinion in International Patent Appln. No. PCT/JP2013/054061.

* cited by examiner

F I G. 1
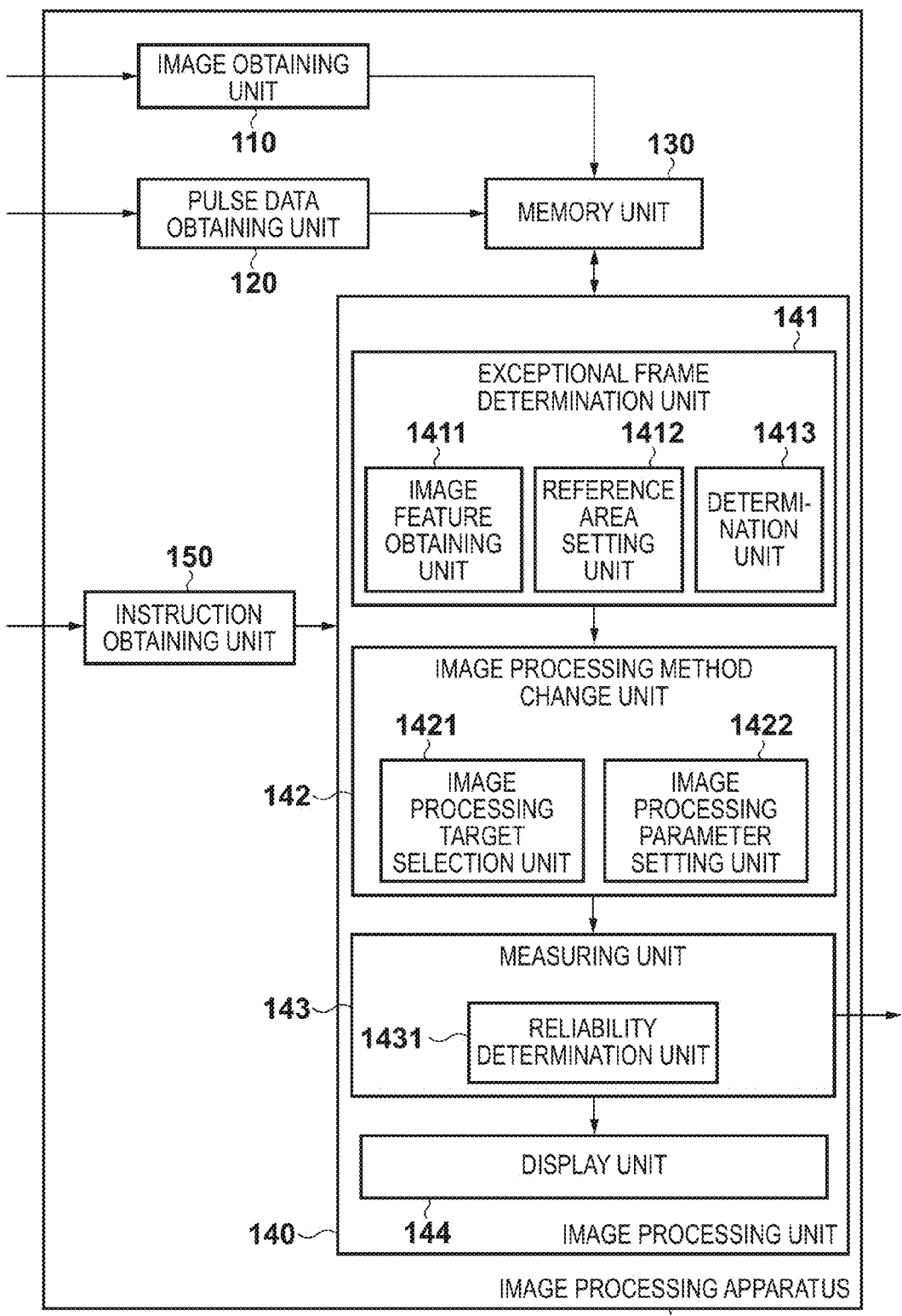

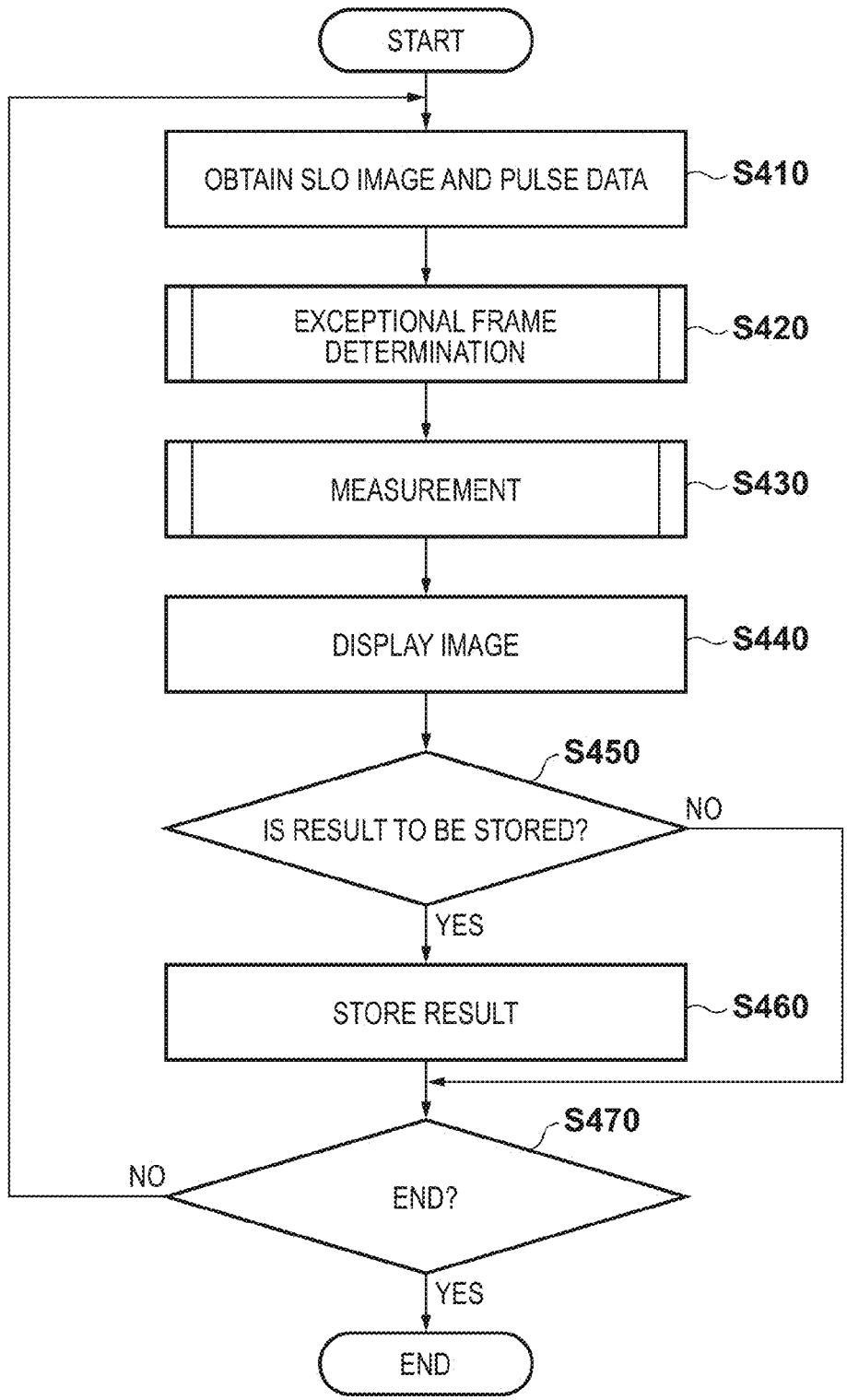

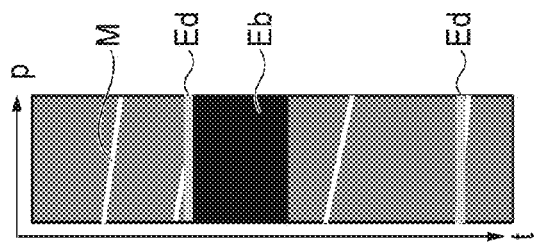
FIG. 5A
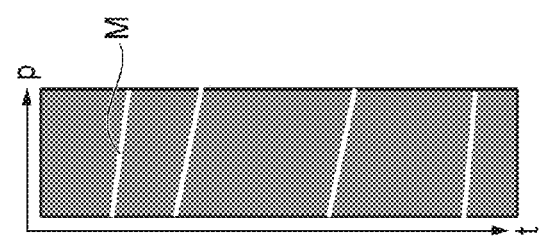
FIG. 5B
FIG. 5C
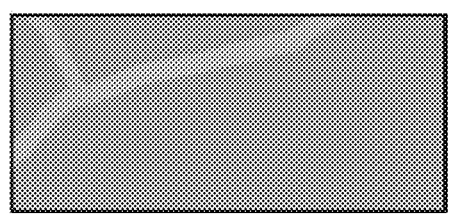
FIG. 5D
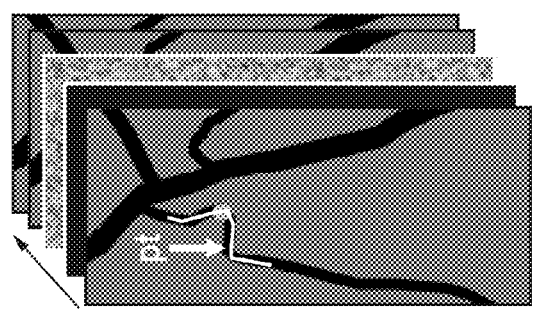
FIG. 5E
FIG. 5F
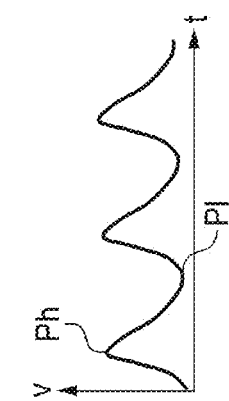
FIG. 5G

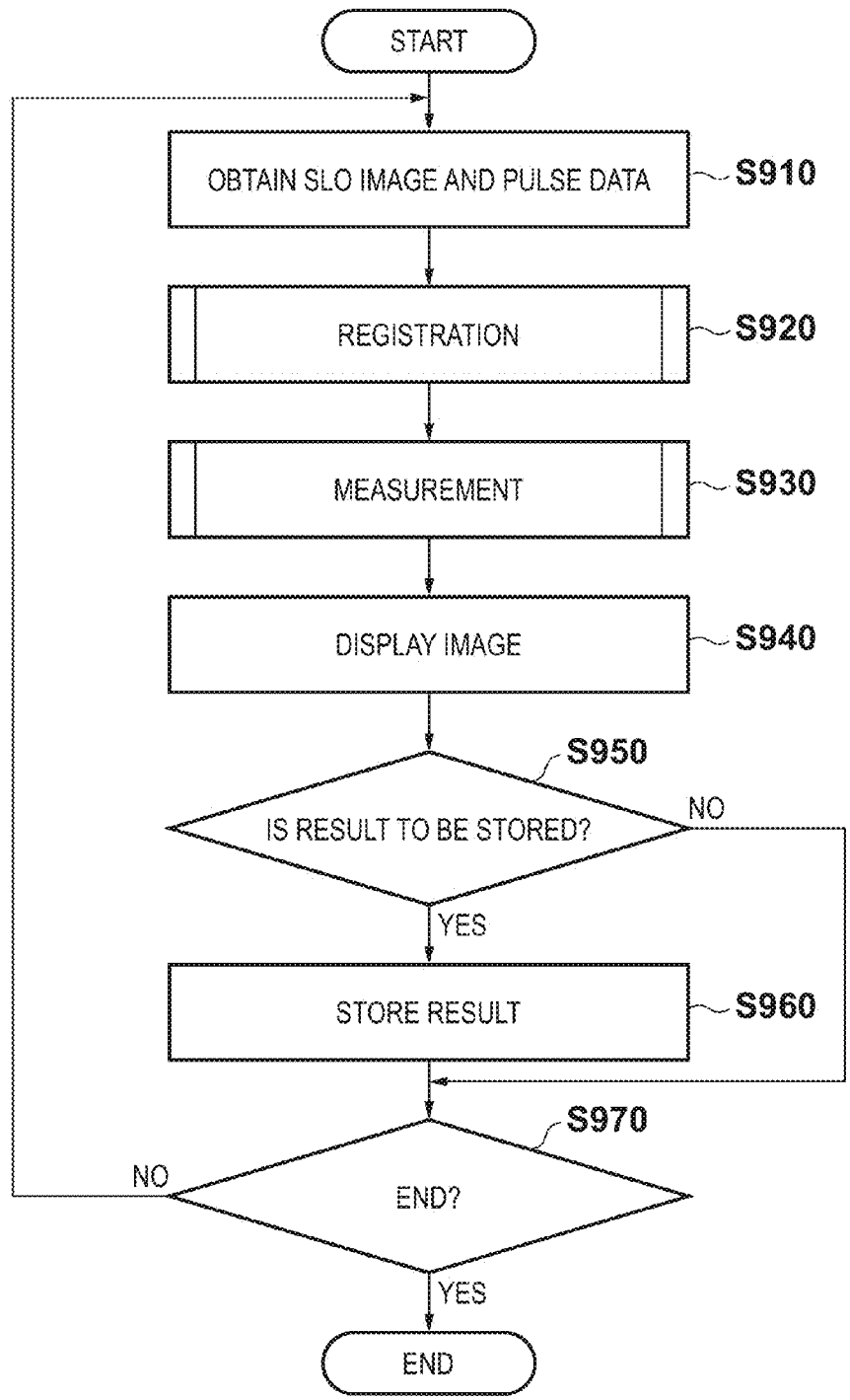

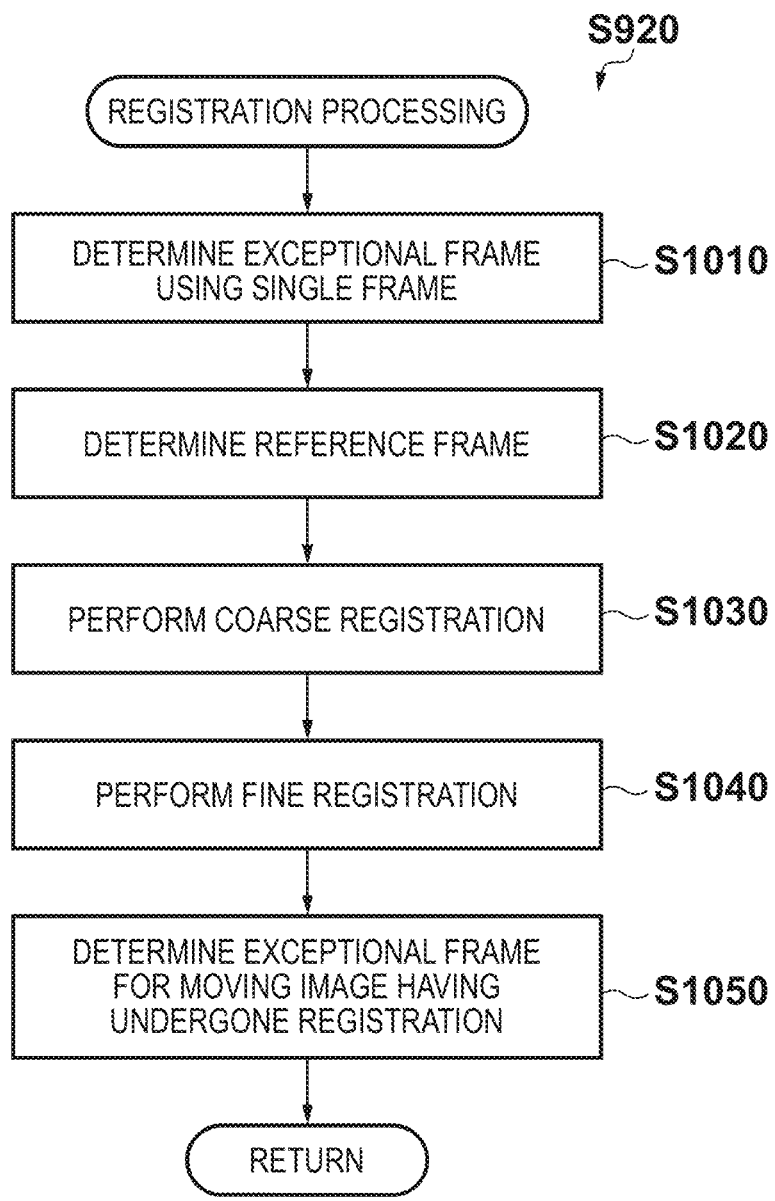

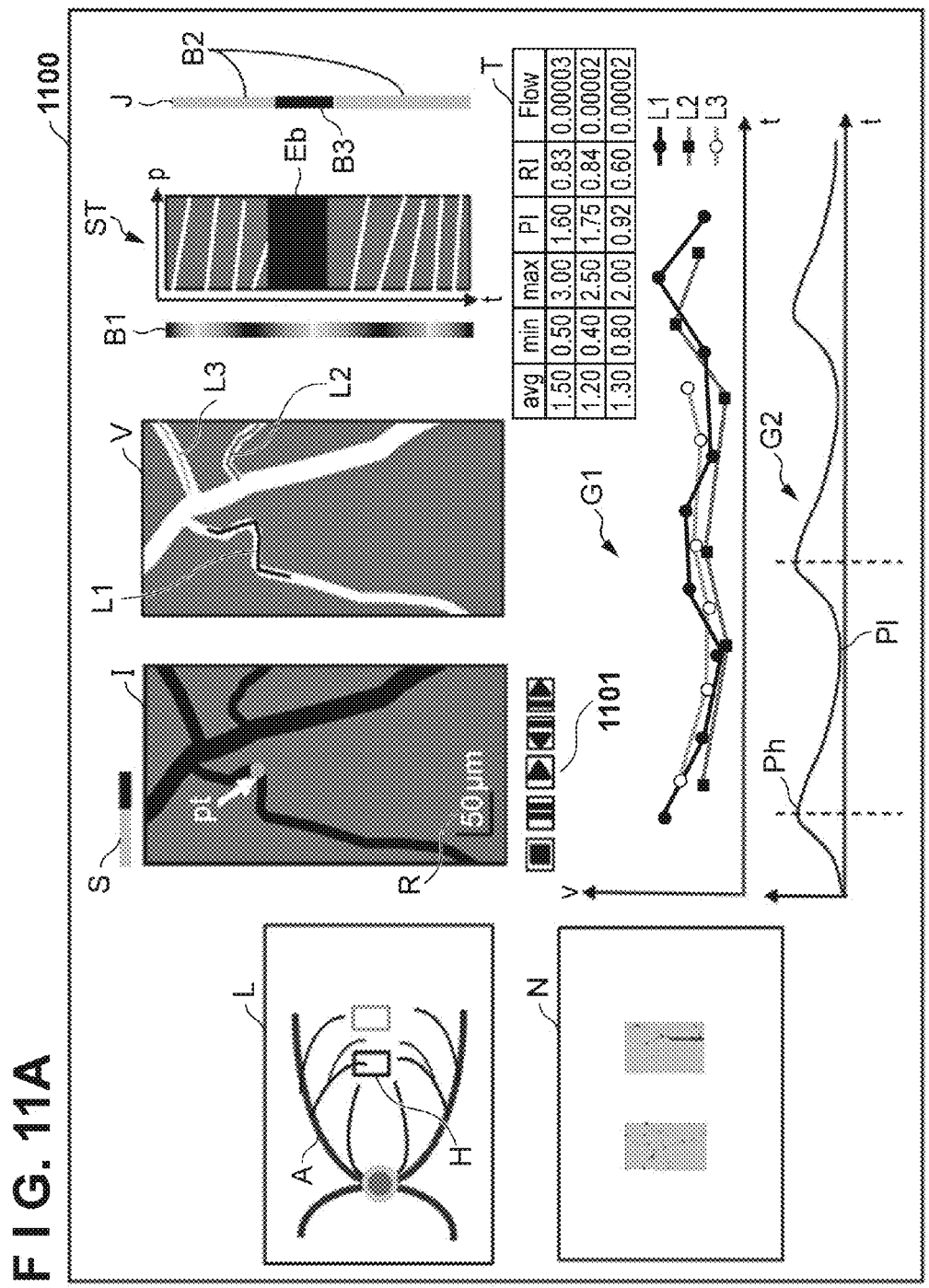

IMAGE PROCESSING APPARATUS AND IMAGE PROCESSING METHOD

TECHNICAL FIELD

The present invention relates to an image processing apparatus and an image processing method and, more particularly, to an image processing apparatus and image processing method suitable for ophthalmic care.

BACKGROUND ART

Examination of an eye portion is widely performed for the purpose of preemptive medical care for lifestyle-related diseases and other diseases that are major causes of blindness. A scanning laser ophthalmoscope (SLO) serving as an ophthalmic apparatus based on the principle of a confocal laser microscope performs raster scanning on a fundus with a laser beam serving as measurement light, and quickly obtains a high-resolution planar image based on the light intensity of the return beam. Such an apparatus for capturing a planar image will be referred to as a SLO apparatus hereinafter.

In recent years, it has become possible to obtain a planar image of a retina with an improved lateral resolution by increasing the beam size of measurement light in a SLO apparatus. As the beam size of measurement light increases, however, the resolution and SN ratio of a planar image decrease due to aberration of an eye to be examined in obtaining a planar image of a retina.

To solve the problem, an adaptive optics SLO apparatus has been developed that includes an adaptive optics for causing a wavefront sensor to measure the aberration of an eye to be examined in real time, and causes a wavefront correction device to correct the aberration of measurement light and to examine the return beam occurring in the eye. Such an adaptive optics SLO apparatus can obtain a high-lateral resolution planar image.

Furthermore, it is possible to obtain such a high-lateral resolution planar image as a moving image (to be referred to as a SLO moving image hereinafter), thereby enabling to noninvasively measure, for example, the hemodynamics of retinal capillaries. More specifically, an image of luminance variations in the frame direction at each x-y position of a SLO moving image is obtained, and retinal capillaries are extracted (FIG. 5B), thereby determining a blood flow velocity measurement position. After that, the measurement position (denoted by a reference symbol pt in FIG. 5A) is specified on the SLO moving image to generate a curved cross-sectional image (FIG. 5D) called a time-space image on the path. The movement locus of blood cells is detected from the time-space image, and a blood cell moving speed is measured based on the angle of the locus.

In the above blood flow measurement processing, an exceptional frame for which measurement processing is difficult due to differences in image features caused by an imaging apparatus or the influence of eye/eyelid movement may occur. Especially for a diseased eye, in many cases, a low luminance frame may occur due to blinking as shown in FIG. 5A, and a frame obtained by capturing an area other than an imaging target area may occur due to fixation disparity. Furthermore, a moving image may include a frame with a low SN ratio due to the characteristics of an apparatus such as an aberration correction failure. If measurement processing is performed without consideration of the influence of such exceptional frames, an image of blood vessels blurs in extracting the blood vessels as shown in FIG. 5C, thereby disabling to specify the positions of the specific blood vessels. Alternatively, in some cases, as denoted by reference symbols Eb and Ed in FIG. 5E, information of a low luminance area or different imaging position is contained in the time-space image due to blinking or fixation disparity, and the locus of blood cells to be measured breaks, thereby making it difficult to detect the movement locus of the blood cells.

To prevent an exceptional frame from occurring in a SLO moving image, there is provided a method of including, in an apparatus, a tracking mechanism for preventing an exceptional frame from occurring in an imaging operation. It is, however, necessary to additionally provide an arrangement for capturing a wide field of view SLO image. Even if such a tracking mechanism is provided, a complete tracking operation is actually difficult when involuntary eye movement during fixation is large.

A technique is required to automatically determine exceptional frames in a SLO moving image to perform image measurement by excluding the exceptional frames or to perform image measurement by changing an image processing method in frames close to the exceptional frames. Japanese Patent Laid-Open No. 2007-330582 (to be referred to as literature 1 hereinafter) describes, as a method of measuring a blood flow velocity in an eye portion moving image, a technique of specifying the start and end points of a blood vessel of the fundus, and obtaining a blood flow velocity based on the time difference in luminance between the start and end points.

In the technique described in literature 1, however, it is necessary to correctly irradiate a blood vessel portion with a beam. If the fundus moves, it is impossible to measure a blood flow velocity. Literature 1 does not consider a case in which a SLO moving image includes a frame obtained when the fundus moves.

Furthermore, a technique of extracting blood capillaries based on the standard deviation of the luminance values between moving image frames of an aberration correction SLO moving image is described in J. Tam et al. "Noninvasive Visualization and Analysis of Parafoveal Capillaries in Humans", IOVS, Vol. 51, No. 3, pp. 1691-1698, 2010 (to be referred to as literature 2 hereinafter). In literature 2, since the standard deviation of the luminance values is obtained using all the frames, an image of blood vessels blurs when the fundus moves (the value of the standard deviation becomes large due to a factor other than movement of blood cells). That is, literature 2 does not consider a technique of correctly extracting blood capillaries when a frame obtained when the fundus moves is included, either.

SUMMARY OF INVENTION

According to an embodiment of the present invention, it is possible to correctly extract a tissue or to robustly measure cell kinetics even if a moving image includes an exceptional frame in which it is difficult to measure the shape of the tissue and the cell kinetics.

According to one embodiment of the present invention, there is provided an image processing apparatus comprising: determination means for determining an exceptional frame of a plurality of frames forming a moving image captured by an ophthalmic apparatus including an aberration correction device; and processing means for applying image processing of a blood vessel area for a frame, among the plurality of frames, which has not been determined as the exceptional frame.

Also, according to another embodiment of the present invention, there is provided an image processing method for an image processing apparatus, comprising the steps of: determining an exceptional frame of a plurality of frames forming a moving image based on an image feature of each frame; and processing the moving image by applying different image processes to the exceptional frame and a non-exceptional frame other than the exceptional frame of the plurality of frames.

Further features of the present invention will become apparent from the following description of exemplary embodiments with reference to the attached drawings.

BRIEF DESCRIPTION OF DRAWINGS

FIG. 1 is a block diagram showing an example of the functional arrangement of an image processing apparatus according to the first embodiment;

FIG. 4 is a flowchart illustrating processing executed by the image processing apparatus according to the first embodiment;

FIGS. 5A to 5G are views for explaining contents of image processing according to the first embodiment;

FIG. 9 is a flowchart illustrating processing executed by the image processing apparatus according to the second embodiment;

FIG. 10 is a flowchart illustrating registration processing according to the second embodiment;

FIG. 11A is a view showing an example of a display screen for the measurement result of a SLO moving image;

DESCRIPTION OF EMBODIMENTS

Preferred embodiments of an image processing apparatus and a method according to the present invention will be described in detail below with reference to the accompanying drawings. Note that the present invention is not limited to the following embodiments.

First Embodiment

In the following embodiment, a case in which the shape of a retinal capillary of an eyeball is measured as the shape of tissue, and movement of blood cells in the retinal capillary is measured as cell kinetics will be exemplified. An image processing apparatus according to the first embodiment detects an exceptional frame including blinking, fixation disparity, or an aberration correction failure from a plurality of frames forming a SLO moving image D, and extracts the retinal capillary or measures a blood cell moving speed by changing an image processing method for the exceptional frame.

More specifically, the image processing apparatus has a functional arrangement shown in FIG. 1. An exceptional frame determination unit 141 determines an exceptional frame based on image features included in the SLO moving image. The exceptional frame determination unit 141 also determines the type and degree of an exception, and an image processing method change unit 142 determines based on the type and degree of the exception whether the exceptional frame contains information about measurement targets (a blood vessel and blood cells). If it is determined that information about measurement targets remains, an image processing parameter setting unit 1422 changes image processing parameters in the exceptional frame, and then extracts a blood vessel or detects the locus of blood cells. On the other hand, if it is determined that no information about measurement targets remains, an image processing target selection unit 1421 selects only a non-exceptional frame, and extracts a blood vessel or detects the locus of blood cells, thereby estimating the blood cell moving speed in the exceptional frame by interpolating measurement data in the non-exceptional frame. A display unit 144 displays the measurement value, the estimated value, and the reliability of the measurement value determined by a reliability determination unit 1431. With the above arrangement, it is possible to robustly extract a blood vessel or measure blood cell kinetics even if an eye portion moving image includes an exceptional frame which is inappropriate for measuring blood cell kinetics or the shape of a blood vessel.

Figure 2:
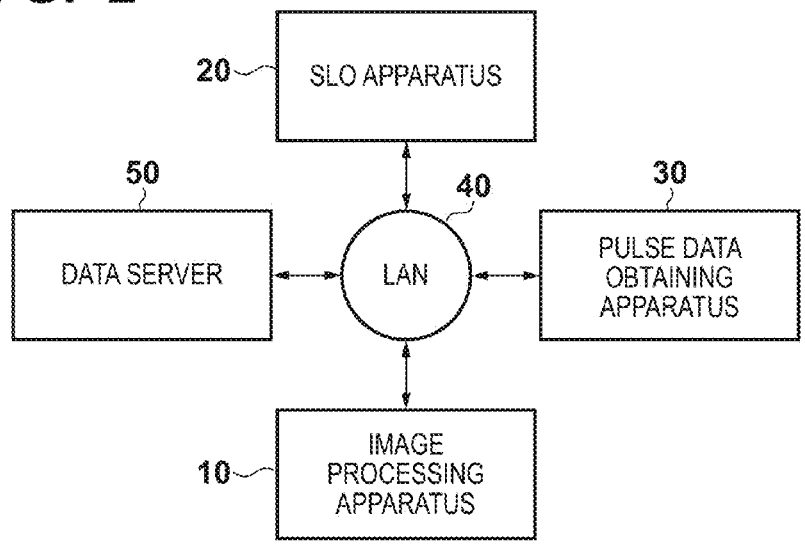
FIG. 2 is a block diagram showing an example of the configuration of a system including the image processing apparatus.

FIG. 2 is a block diagram showing the configuration of an imaging system including an image processing apparatus 10 according to the first embodiment. As shown in FIG. 2, the image processing apparatus 10 is connected with a SLO apparatus 20, a pulse data obtaining apparatus 30, and a data server 50 via a local area network (LAN 40) formed by an optical fiber, a USB, IEEE1394, or the like. Note that the apparatus 10 may be connected with these apparatuses via an external network such as the Internet. One apparatus may implement some of the image processing apparatus 10, SLO apparatus 20, pulse data obtaining apparatus 30, and data server 50. For example, one information processing apparatus may include the image processing apparatus 10 and data server 50.

The SLO apparatus 20 serves as an adaptive optics scanning laser ophthalmoscope (AO-SLO), and captures the planar image (AO-SLO moving image) of a fundus region. The SLO apparatus 20 captures the SLO moving image D, and transmits, to the image processing apparatus 10 and data server 50, the SLO moving image D and information about a fixation target position F used to capture it. The SLO apparatus 20 includes an SLD (Super Luminescent Diode), a Shack-Hartmann wavefront sensor, adaptive optics, first and second beam splitters, an X-Y scanning mirror, a focusing lens, an aperture stop, an optical sensor, an image forming unit, and an output unit. Light emitted by the SLD serving as a light source is reflected by the fundus. Some of the reflected light is incident on the Shack-Hartmann wavefront sensor through the second beam splitter, and the remaining light is incident on the optical sensor through the first beam splitter. The Shack-Hartmann wavefront sensor is a device for measuring the aberration of an eye, and a CCD is connected to a lens array. When the incident light passes through the lens array, a luminescent spot group appears in the CCD, thereby measuring wave aberration based on misregistration of the projected luminescent spots. Based on the wave aberration measured by the Shack-Hartmann wavefront sensor, the adaptive optics drives an aberration correction device (a deformable mirror or spatial light phase modulator) to correct the aberration. The light having undergone the aberration correction enters the optical sensor through the focusing lens and aperture stop. It is possible to control a scanning position on the fundus by moving the X-Y scanning mirror, thereby obtaining data for a time (frame rate×number of frames) and an imaging target area specified in advance by an operator. The data is transmitted to the image forming unit, which forms image data (a moving image or still image) by correcting image distortion due to a variation in scanning speed or correcting luminance values. The output unit outputs the image data formed by the image forming unit. To focus on a specific depth position on the fundus, it is possible to perform at least one of adjustment using the aberration correction device of the adaptive optics and adjustment by arranging a focus adjustment lens (not shown) in the optics and moving the lens. Note that it is possible to use an ophthalmic apparatus such as a fundus camera including adaptive optics or an aberration correction device, instead of the SLO apparatus 20.

The pulse data obtaining apparatus 30 is used to obtain biomedical signal data (pulse data) which autonomously changes, and includes, for example, a sphygmograph or electrocardiograph. In response to an operation by an operator (not shown), the pulse data obtaining apparatus 30 obtains pulse data P as well as the SLO moving image D. Note that the pulse data P is represented as a sequence of points having the abscissa indicating an obtaining time t and the ordinate indicating a pulse wave signal value v measured by the sphygmograph, as shown in FIG. 5F. The obtained pulse data P is transmitted to the image processing apparatus 10 and data server 50.

The data server 50 holds imaging condition data such as the SLO moving image D of the eye to be examined and the fixation target position F, the pulse data P, and the image features of the eye portion. The data server 50 stores the SLO moving image D and fixation target position F output from the SLO apparatus 20, the pulse data P output from the pulse data obtaining apparatus 30, and the image features of the eye portion output from the image processing apparatus 10. Furthermore, in response to a request from the image processing apparatus 10, the data server 50 transmits the SLO moving image D, the pulse data P, the image features of the eye portion and the normal value data of the image features to the image processing apparatus 10.

Figure 3:
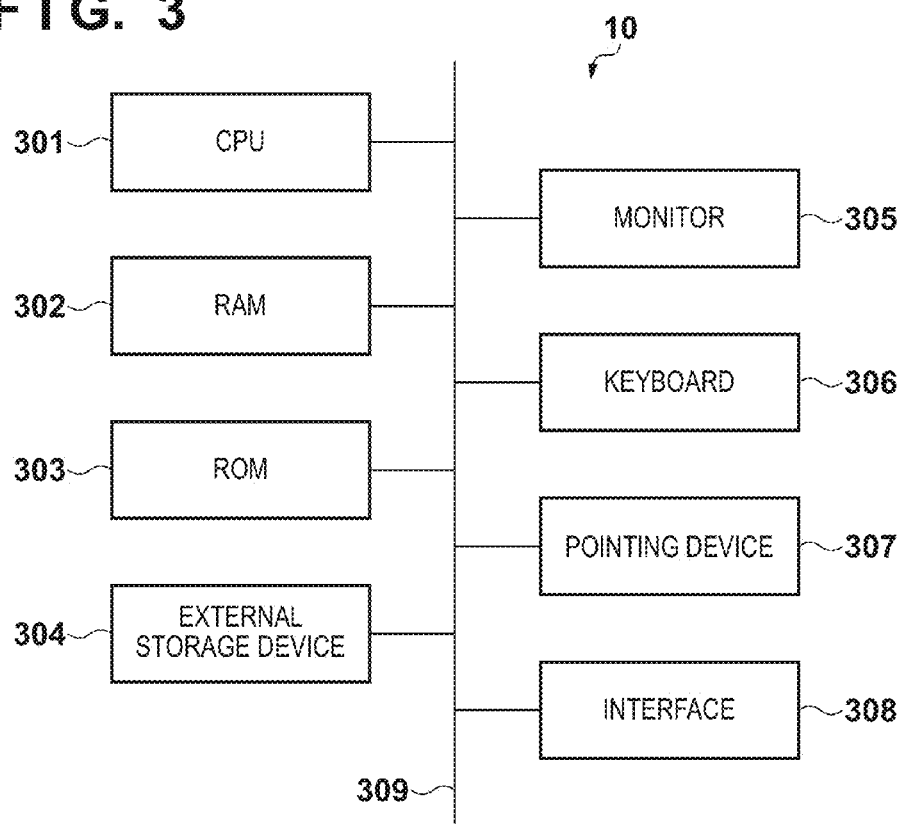
FIG. 3 is a block diagram showing an example of the hardware arrangement of a computer for implementing the image processing apparatus.

The hardware arrangement of the image processing apparatus 10 according to this embodiment will be described with reference to FIG. 3. Referring to FIG. 3, reference numeral 301 denotes a central processing unit (CPU); 302, a memory (RAM); 303, a control memory (ROM); and 304, an external storage device. A monitor 305 performs various displays under the control of the CPU 301. Reference numeral 306 denotes a keyboard; 307, a pointing device (for example, a mouse) with which the user inputs an operation; and 308, an interface which connects the LAN 40 and image processing apparatus 10 with each other. The external storage device 304 stores control programs for implementing an image processing function according to the embodiment, and data to be used to execute the control programs. The control programs and data are loaded, as needed, into the RAM 302 via a bus 309 under the control of the CPU 301, and executed by the CPU 301, thereby functioning as each unit to be explained below with reference to FIG. 1 and the like.

FIG. 1 is a block diagram showing the functional arrangement of the image processing apparatus 10. Referring to FIG. 1, the image processing apparatus 10 includes an image obtaining unit 110, a pulse data obtaining unit 120, a memory unit 130, an image processing unit 140, and an instruction obtaining unit 150. The image processing unit 140 includes the exceptional frame determination unit 141, the image processing method change unit 142, a measuring unit 143, and a display unit 144. The exceptional frame determination unit 141 includes an image feature obtaining unit 1411, a reference area setting unit 1412, and a determination unit 1413. The image processing method change unit 142 includes the image processing target selection unit 1421 and the image processing parameter setting unit 1422. Furthermore, the measuring unit 143 includes the reliability determination unit 1431. The function of each block of the image processing apparatus 10 will be described below in association with the practical execution procedure of the image processing apparatus 10 shown in the flowchart of FIG. 4.

<Step S410> The pulse data obtaining unit 120 requests the pulse data obtaining apparatus 30 to obtain pulse data P on a biomedical signal. In this embodiment, a plethysmograph is used as the pulse data obtaining apparatus 30 to obtain the pulse wave data P from an ear lobe of an object. In response to the obtaining request from the pulse data obtaining unit 120, the pulse data obtaining apparatus 30 obtains the corresponding pulse data P and transmits it. After that, the pulse data obtaining unit 120 can receive the pulse wave data P via the LAN 40 from the pulse data obtaining apparatus 30 as a response to the obtaining request. The pulse data obtaining unit 120 stores the received pulse data P in the memory unit 130.

The image obtaining unit 110 requests the SLO apparatus 20 to obtain a SLO moving image D captured at a fixation target position F, and the fixation target position F. In this embodiment, the SLO apparatus 20 obtains the SLO moving image D by setting the fixation target position F at the parafovea of a macular region. Note that the imaging position setting method is not limited to this, and an imaging position may be set at an arbitrary position. There are a case in which the image obtaining unit 110 starts obtaining the SLO moving image D according to a given phase of the pulse data P obtained by the pulse data obtaining apparatus 30, and a case in which obtaining of the pulse wave data P and SLO moving image D starts immediately after the request to obtain the SLO moving image D is sent. In this embodiment, the latter case (obtaining of the pulse data P and the SLO moving image D starts immediately after the request to obtain the SLO moving image D is sent) is considered.

In response to the obtaining request from the image obtaining unit 110, the SLO apparatus 20 obtains the SLO moving image D and the fixation target position F and transmits them. The image obtaining unit 110 receives the SLO moving image D and the fixation target position F from the SLO apparatus 20 via the LAN 40. The image obtaining unit 110 stores the received SLO moving image D and fixation target position F in the memory unit 130. Note that in this embodiment, the SLO moving image D is a moving image having undergone inter-frame registration.

<Step S420> The exceptional frame determination unit 141 obtains image features from each frame Di (i=1, . . . , n0) of the SLO moving image D, and performs exceptional frame determination (determines whether the frame is an exceptional frame, and the type and degree of an exception) using the obtained image features. A frame with a smallest frame number among the frames other than the exceptional frames is set as a reference frame. Furthermore, exceptional frame determination is performed based on the inter-frame displacement amount of the image feature group obtained from each frame. The practical procedure of image feature obtaining processing and exceptional frame determination processing using a single frame will be described in detail with reference to steps S610 and S620 of FIG. 6. Note that the reference frame setting operation is not limited to the above one, and an arbitrary frame other than the exceptional frames may be specified as a reference frame, or a reference frame may be automatically selected based on specific image features.

<Step S430> Based on the information on the type and degree of each exceptional frame of the SLO moving image D, the image processing method change unit 142 determines, for the exceptional frame, whether to use luminance information in the exceptional frame to measure blood cell kinetics. For an exceptional frame for which it has been determined to use the luminance information, the image processing parameter setting unit 1422 changes image processing parameters for the exceptional frame, and performs measurement. On the other hand, for a frame for which it has been determined not to use the luminance information, the image processing target selection unit 1421 selects a frame other than the exceptional frame as a measurement target frame, and then extracts a blood vessel and measures a blood flow. Note that the method of changing the image processing parameters will be described in detail later with reference to a flowchart (step S730) shown in FIG. 7.

When calculating a blood flow velocity, a relative velocity value within one cycle of a pulse wave is calculated using pulse data. The method of calculating the velocity value will be described with reference to the flowchart (step S750) shown in FIG. 7. Furthermore, the reliability determination unit 1431 determines the reliability of a measurement result based on information about the exceptional frame number and the type or degree of the exception. The method of determining the reliability of the measurement data will be described with reference to the flowchart (step S760) of FIG. 7.

<Step S440> The display unit 144 displays, on the monitor 305, an image showing a blood vessel area specified in step S430 and the measurement result of a blood cell moving speed within the specified blood vessel area, or the reliability of the measurement data determined by the reliability determination unit 1431. For example, the display unit 144 displays, in an edge portion of the blood vessel area image, information about the number of images used for the blood vessel extraction operation. The reliability of a velocity value or speed map obtained based on a locus passing through an exceptional frame among blood cell loci detected on the time-space image is displayed as a score (a numerical value) or in color. Note that the display method is not limited to this, and an arbitrary display method may be used.

<Step S450> The instruction obtaining unit 150 obtains an instruction indicating whether to store, in the data server 50, the SLO moving image D, the fixation target position F, the exceptional frame number sequence, and the analysis data (extreme values and cycle) of the pulse wave which are displayed in step S440. The operator inputs the instruction via, for example, the keyboard 306 or pointing device 307. If a storage operation is instructed, the process advances to step S460; otherwise, the process advances to step S470.

<Step S460> The image processing unit 140 transmits, to the data server 50, an examination date/time, information for identifying an eye to be examined, the SLO moving image D and the fixation target position F of the image group, the exceptional frame number sequence, and the analysis data of the pulse wave in association with each other.

<Step S470> The instruction obtaining unit 150 obtains an instruction indicating whether to terminate the display processing of the SLO moving image D by the image processing apparatus 10. The operator inputs the instruction via the keyboard 306 or pointing device 307. If the unit 150 obtains an instruction to terminate the processing, the analysis processing ends. On the other hand, if the unit 150 obtains an instruction to continue the processing, the process returns to step S410 to execute processing for a next eye to be examined (or re-execute processing for the same eye to be examined).

Figure 6:
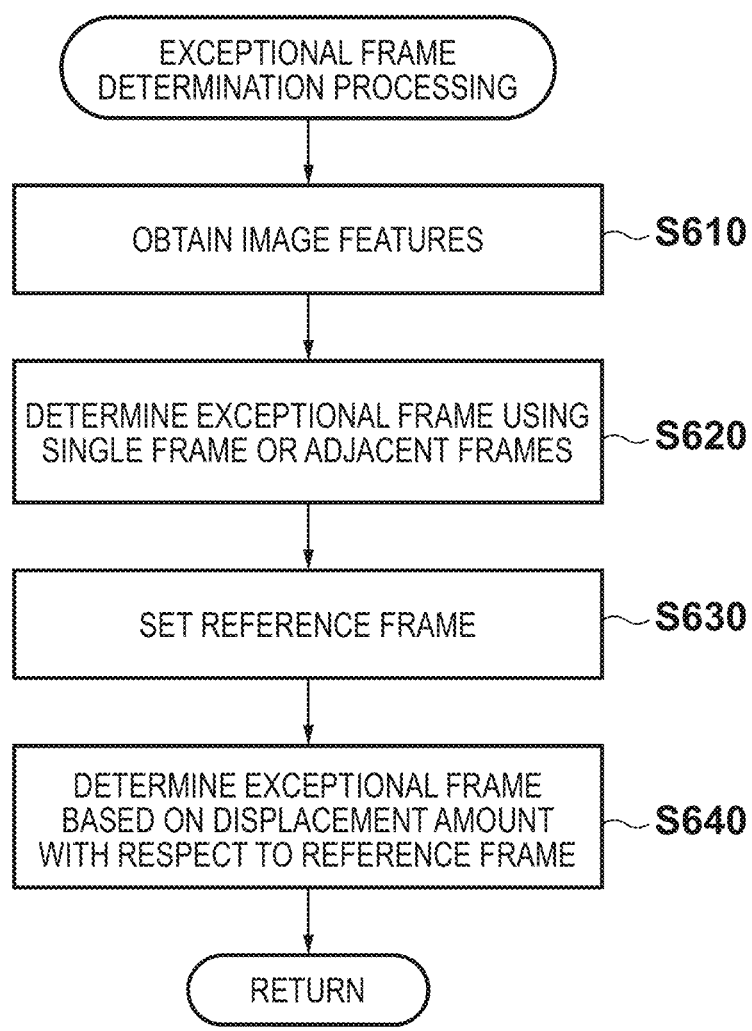
FIG. 6 is a flowchart illustrating exceptional frame determination processing according to the first embodiment.

The exception determination processing executed in step S420 will now be described with reference to FIG. 6.

<Step S610> The image feature obtaining unit 1411 obtains image features from the SLO moving image D. Although arbitrary image features can be used, an average luminance value Ai, a signal to noise ratio (SN ratio), and a blood vessel area Vi in each frame Di of the SLO moving image D are obtained in this embodiment. An arbitrary known blood vessel extraction method can be used as a blood vessel area obtaining method, and in this embodiment, an area where a luminance value is equal to or smaller than a threshold T1 is obtained. Furthermore, an intersection portion Cin (n=1, . . . , n4≥3) of a sequence of points Bim (m=1, 2, . . . , n3) obtained by thinning the blood vessel area Vi is also obtained.

<Step S620> The exceptional frame determination unit 141 determines an exceptional frame based on the image features of one frame and/or the change amount in image feature between adjacent frames. For example, the exceptional frame determination unit 141 detects, from the frames Di of the SLO moving image D, as an exceptional frame, a frame where the luminance is extremely low (a luminance error has occurred) due to blinking, a frame where image distortion has occurred (a distance change amount between feature points is large) due to involuntary eye movement during fixation, or a frame where the SN ratio is low due to an aberration correction failure.

Furthermore, the type (luminance error/image distortion/low SN ratio) and degree of an exception in the exceptional frame are determined.

To detect an exceptional frame as described above, the following determination operations are executed.

If the average luminance value Ai of a frame i of the SLO moving image D is equal to or smaller than a threshold T2, the frame i is determined as an exceptional frame. In this case, the type of exception is determined as "luminance error", and the degree of the exception is determined as "the luminance value".

If a difference, between adjacent frames, in value of the sum of squares of the distance between the blood vessel intersection portions Cin of the frame i of the SLO moving image D is equal to or larger than a threshold T3, the frame i is determined as an exceptional frame. This is a case in which the intersection portion Cin is used as a distance change amount between feature points to determine image distortion due to involuntary eye movement during fixation. In this case, the type of exception is determined as "image distortion", and the degree of the exception is determined as "the difference, between adjacent frames, in value of the sum of squares of the distance between the blood vessel intersection portions Ci".

If the SN ratio of the frame i of the SLO moving image D is equal to or smaller than a threshold T4, the frame i is determined as an exceptional frame. In this case, the type of exception is determined as "low image quality", and the degree of the exception is determined as "the SN ratio".

Note that the exceptional frame determination method is not limited to them, and an arbitrary exception determination method can be used. For example, the luminance statistic (average value, mode, or maximum value) of a differential image obtained by executing differential processing for each frame is calculated. If the luminance statistic is equal to or smaller than a threshold T5, it may be considered that the frame blurs due to movement of an object, thereby determining the frame as an exceptional frame. Note that the type of exception in this case is, for example, "blurring", and the degree of the exception is, for example, "the luminance statistic". Alternatively, the exceptional frame determination unit 141 may determine, as an exceptional frame, a frame which includes no specific part, tissue, cell, or lesion, or includes not more than a given proportion of it. In this case, the image processing automatically detects, from each frame, a specific part, tissue, cell, or lesion, and measures its size. In this case, the type of exception is, for example, "specific part loss", and the degree of the exception is, for example, "the size (number of pixels) of the specific area in the frame".

<Step S630> The reference area setting unit 1412 sets a reference area for determining a fixation disparity frame (exceptional frame) in the moving image D. In this embodiment, the unit 1412 sets, as a reference area, a frame with a smallest frame number as a whole among frames other than those which have been determined as exceptional frames in step S620.

Note that the reference area setting method is not limited to this, and an arbitrary setting method can be used. For example, the unit 1412 may obtain a reference frame number specified by the user from the instruction obtaining unit 150, and set, as a reference area, the whole frame corresponding to the specified reference frame number. Alternatively, the unit 1412 may set, as a reference area, an area specified by the user within the above reference frame. Alternatively, the image feature obtaining unit 1411 may use an arbitrary known image processing method to detect a part (central fovea) or lesion, and then the unit 1412 may set, as a reference area, the part or lesion area detected in a non-exceptional frame with a smallest frame number.

<Step S640> The exceptional frame determination unit 141 determines, as an exceptional frame, a frame where the shift between the reference area set in step S630 and an area corresponding to the reference area is large. The exceptional frame determination unit 141, for example, calculates a displacement amount between an image feature (for example, the blood vessel intersection portion Cin) in the reference area set in step S630 and that in a non-reference area, and then determines, as an exceptional frame, a frame where the displacement amount is larger than a tolerance value.

In this embodiment, as the displacement amount of the frame i with respect to the reference frame, a displacement amount vector (x, y, θ, sx, sy) having, as its components, a translation (x, y), rotation θ, and magnification (sx, sy) is defined. If at least one of x>Tx, y>Ty, θ>Tθ, sx>Tsx, and sy>Tsy holds, the frame i is determined as an exceptional frame. For such an exceptional frame, "fixation disparity" is set as the type of exception, and "displacement amount (vector)" is set as the degree of the exception.

Note that the definition of the displacement amount is not limited to this, and an arbitrary value may be used as long as it represents the degree of displacement (scalar quantity or vector quantity). A proportion of the reference area to be observed/measured which is included in each frame, for example, (area of whole reference area)/(area of reference area included in each frame Di) may be defined as a displacement amount.

Figure 7:
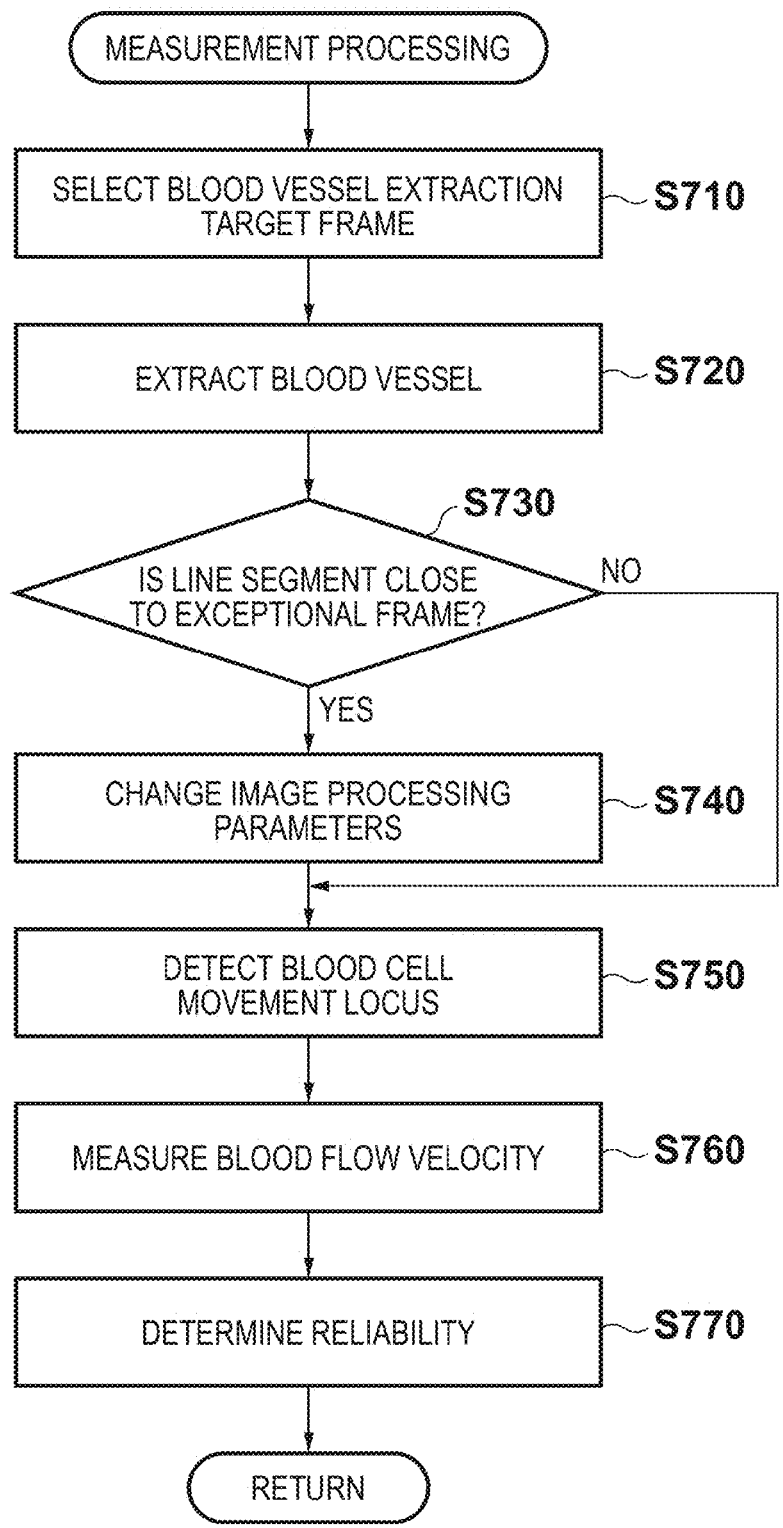
FIG. 7 is a flowchart illustrating measurement processing according to the first embodiment.

The measurement processing executed in step S430 will be described with reference to the flowchart shown in FIG. 7.

<Step S710> The image processing target selection unit 1421 selects a frame to be used for blood vessel extraction processing. In this embodiment, the unit 1421 selects a frame to be used for blood vessel extraction processing based on the exceptional frame determination result in step S420. Note that in the blood vessel extraction processing, it is possible to correctly extract details of blood capillaries by selecting as many images as possible where a change in luminance due to movement of blood cells is clearly observed, and then executing extraction processing. In the blood vessel extraction processing, therefore, all non-exceptional frames are selected as image processing targets.

<Step S720> The measuring unit 143 extracts, as a blood vessel area, an area where the variance of luminance values in the frame direction at each x-y position (pixel) on the frames selected in step S710 is equal to or larger than a given value. This processing uses the nature in which within the blood vessel area, the luminance is high when white blood cells pass through, and the luminance is low in other cases. As a result, the blood vessel area is specified as a set of blood cell movement loci. Note that although the above-described processing does not use exceptional frames to extract the blood vessel area, the present invention is not limited to this. According to the degree of an exception obtained for an exceptional frame, "the given value" to be compared with the variance may be changed.

<Step S730> The image processing parameter setting unit 1422 changes parameters forming an equation for a straight line candidate when generating a time-space image with the abscissa representing the blood vessel position and the ordinate representing the time, and detecting, as a straight line, a blood cell movement locus in the time-space image. Note that the blood vessel position is a position on a path Pt in FIG. 5A. In this embodiment, since a straight line is detected in the time-space image using the Hough transform, a straight line candidate passing through coordinates (x, y) is represented (θ and ρ are changed) by:

$$x \cos θ + y \sin θ = ρ \qquad (1)$$

If a straight line candidate represented by equation (1) can pass through an exceptional frame (a line segment is close to the exceptional frame on the time-space image), the process advances to step S740. If a straight line candidate does not pass through an exceptional frame (a line segment is not close to the exceptional frame on the time-space image), the process advances to step S750. Note that a frame close to an exceptional frame on the time-space image indicates a frame existing within a predetermined time range from the time of the exceptional frame. A time estimated to be required for blood cells to pass through the path Pt can be used as a predetermined time range. Note that it is possible to estimate such a time range based on a general blood cell moving speed.

<Step S740> A luminance value on the time-space image is transformed to a value in a θρ space by the Hough transform, and a combination of θ and ρ with a highest evaluation value in the θρ space is detected as a straight line. If a straight line candidate defined by a combination of θ and ρ can pass through an exceptional frame (for a frame existing within a predetermined time range from the time of the exceptional frame), a vote value in the θρ space is multiplied by a weight w (>1.0). Note that according to the degree of the exception of the nearby exceptional frame, the weight w as a processing parameter may be changed. This enables to robustly detect a blood cell movement locus as a straight line even if part of it is lost due to the influence of the exceptional frame.

<Step S750> The measuring unit 143 detects a blood cell movement locus using the image processing parameter changed in step S740. Although an arbitrary line detection method can be used, a blood cell movement locus is detected using the Hough transform in this embodiment.

Note that the method of detecting a blood cell movement locus is not limited to the above one, and an arbitrary method may be used. For example, a blood cell locus may be detected as a curve using a deformable model. In this case, if the type of exception in the exceptional frame is "low SN" and the value of the SN ratio falls within the range between thresholds Tx and Ty (information to be measured remains within the exceptional frame), the weight of image energy at an existing control point is increased. As described above, a blood cell locus may be detected by changing the image processing parameter according to the degree of the exception of the exceptional frame.

<Step S760> The measuring unit 143 measures a blood cell moving speed (blood flow velocity) based on the angle of the blood cell movement locus, on the time-space image, detected in step S770. Since the number of white blood cells visually recognized on the SLO moving image D is actually small (about 1% in the blood), the number of straight lines representing the movement loci of the white blood cells detectable on the time-space image is limited. If, therefore, the user wants to analyze a change in blood flow velocity within a cardiac cycle in detail, the number of constituent points in a blood flow velocity graph is not enough.

In this embodiment, using the pulse data P based on a biomedical signal, which has been obtained in capturing the SLO moving image, a phase corresponding to a frame set for which the movement locus or moving speed has been measured is specified. A phase within a cardiac cycle, which corresponds to each frame of the frame set, is obtained using the pulse data P, and blood flow velocity data for a plurality of cardiac cycles are collectively displayed as a blood flow velocity waveform for one cardiac cycle as shown in FIG. 5G by associating a moving speed with the phase. Actually, a phase is divided into small intervals, and the average value of blood flow velocity values within each small interval is obtained. Note that the blood speed measurement method is not limited to this, and a blood flow velocity average value at the timing when pulse data indicates a local minimum (during the telediastolic period) may be calculated.

<Step S770> The reliability determination unit 1431 calculates the reliability of the result of the above-described moving image processing (blood vessel extraction, blood cell movement locus detection, and the like) based on the number of exceptional frames in the frame set used for the processing. The reliability determination unit 1431, for example, determines the reliability of the blood vessel area detected in step S720 and that of the blood cell moving speed calculated in step S760. In the embodiment, the reliability of the blood vessel area extraction and that of the blood cell movement locus are calculated based on the presence of exceptional frames (for example, the number of exceptional frames) in the frame set used. The reliability of the blood vessel area is set by:

(number of non-exceptional frames used to extract blood vessel area)/(total number of frames)

Note that the reliability calculation method is not limited to this, and an arbitrary index may be used.

The reliability of the blood cell movement locus is set by:

(length of actually detected blood cell locus)/(length of straight line passing through exceptional frame+length of actually detected blood cell locus)

Note that the reliability calculation method is not limited to this, and an arbitrary index may be used. For example, a value inversely proportional to the weight w added in step S740 may be obtained as the reliability.

As described above, according to the first embodiment, the image processing apparatus 10 estimates image features and a measurement value in an exceptional frame according to the type and degree of the exceptional frame detected from the SLO moving image D, and changes an image processing parameter around the exceptional frame. This enables to robustly extract a blood vessel and measure blood cell kinetics even if an eye portion moving image includes an exceptional frame which is inappropriate for measuring blood cell kinetics or the shape of a blood vessel.

Second Embodiment

In the first embodiment, exceptional frame determination processing is executed for the SLO moving image D having undergone registration. In the second embodiment, a registration unit 145 (FIG. 8) is additionally arranged, and an exceptional frame is determined from a SLO moving image D using image features obtained in registration processing. This enables to calculate a displacement amount with respect to a reference frame more correctly and efficiently, thereby determining an exceptional frame.

Figure 8:
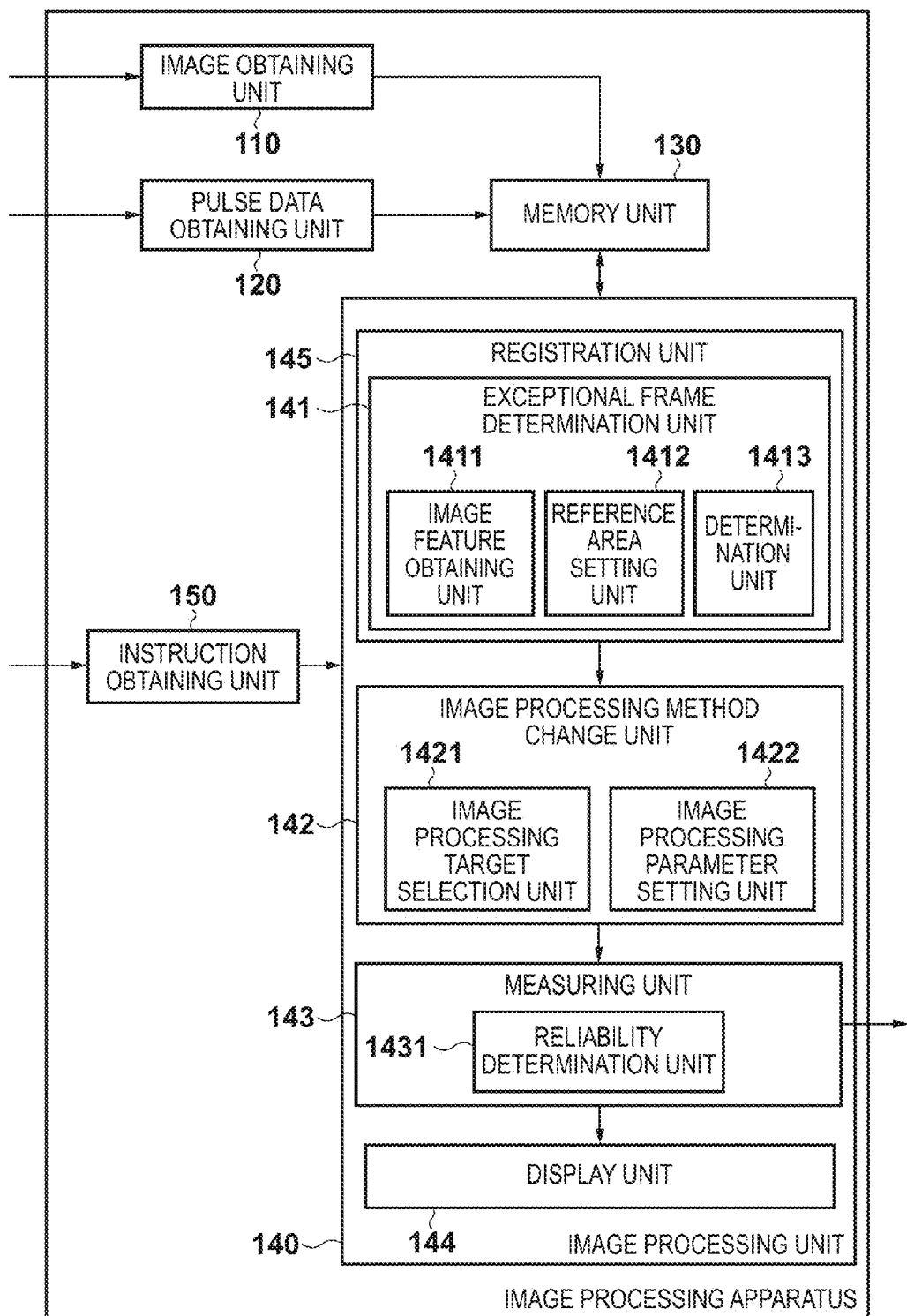
FIG. 8 is a block diagram showing an example of the functional arrangement of an image processing apparatus according to the second embodiment.

FIG. 8 shows an example of the functional arrangement of an image processing apparatus 10 according to the second embodiment. A different point from the functional arrangement (FIG. 1) of the first embodiment is that the registration unit 145 is arranged, and an exceptional frame determination unit 141 is arranged in the registration unit 145. Image processing according to the second embodiment is as shown in the flowchart of FIG. 9, and operations in steps except for step S920 are the same as those in the first embodiment (operations in steps S910 and S930 to S970 of FIG. 9 are the same as those in steps S410 and S430 to S470 of FIG. 4). Processing in step S920 will be described below.

<Step S920> The registration unit 145 reads the SLO moving image D from a memory unit 130, and performs inter-frame registration and exception determination in the SLO moving image D. The processing in step S920 will be described with reference to a flowchart shown in FIG. 10.

<Step S1010> Exceptional frame determination using a single frame (exceptional frame determination using the image features of a single frame) is performed for each frame i of the SLO moving image D. In this embodiment, the exceptional frame determination unit 141 calculates an average luminance value Ai and an SN ratio SNi of each frame i. A luminance error is determined if Ai is equal to or smaller than a threshold T2, and low image quality is determined if the SN ratio SNi is equal to or smaller than a threshold T4, thereby determining the frame as an exceptional frame. Note that the method of determining an exceptional frame for a single frame is not limited to this, and an arbitrary exception determination method may be used.

<Step S1020> The registration unit 145 sets a reference frame as a registration reference. In this embodiment, a frame with a smallest frame number among frames other than those which have been determined as exceptional frames in step S1010 is set as a reference frame. Note that the reference frame setting method is not limited to this, and an arbitrary setting method may be used. For example, the unit 145 may obtain a reference frame number specified by the user from the instruction obtaining unit 150, and set, as a reference frame, a frame corresponding to the specified reference frame number. Alternatively, the unit 145 may obtain specific image features from each frame, and automatically set a reference frame based on the image features.

<Step S1030> The registration unit 145 roughly associates the positions of frames with each other (coarse registration). Although an arbitrary registration method can be used, coarse registration is performed using a correlation coefficient as an inter-image similarity evaluation function and using affine transformation as a coordinate transformation method in this embodiment.

<Step S1040> The registration unit 145 performs fine registration based on data of the coarse position correspondence between frames obtained in step S1030. In this embodiment, the unit 145 performs fine registration between frames using an FFD (Free Form Deformation) method as a non-rigid registration method for the moving image which has undergone coarse registration in step S1030. In this way, all the frames except for the exceptional frames undergo registration with respect to the reference frame. Note that the fine registration method is not limited to this, and an arbitrary registration method may be used.

<Step S1050> Exceptional frame determination is performed for each frame of the moving image which has undergone fine registration in step S1040. In this embodiment, an image feature obtaining unit 1411 of the exceptional frame determination unit 141 calculates the difference between the reference frame and each frame (except for the reference frame), thereby obtaining the histogram of a difference image. If the average value of the histogram is equal to or larger than a threshold T6 and the variance of the histogram is equal to or larger than a threshold T7, the exceptional frame determination unit 141 determines that a different position on the fundus is temporarily captured due to involuntary eye movement during fixation, thereby determining the frame as an exceptional frame.

Note that the exceptional frame determination method is not limited to this, and an arbitrary determination method may be used. For example, for each frame of the moving image having undergone fine registration, extraction of a blood vessel and detection of a blood vessel intersection portion Cin are performed as in the first embodiment. The sum of squares of the distance between the blood vessel intersection portions Cin is obtained in each frame. If the difference in value of the sum of squares of the distance between adjacent frames is equal to or larger than a threshold T3, it is considered that image distortion has occurred, thereby determining the frame as an exceptional frame.

In this embodiment, a combination of registration parameters with which the whole frame of the SLO moving image D is most similar to the reference frame is obtained using pixel value-based inter-image similarity. The present invention, however, is not limited to this. Image features (a part such as a lesion and central fovea, and a feature point such as a branch of a blood vessel) to be observed may be detected in each frame of the SLO moving image D, and frames of the SLO moving image may undergo registration so that the positions of the image features most finely coincide with each other.

Although inter-frame registration in a single SLO moving image has been explained in this embodiment, the present invention is not limited to this. For example, inter-frame registration may be performed in a plurality of SLO moving images Dj obtained by repeatedly capturing an image at almost the same imaging position several times. In this case, a reference frame in a specific one of the plurality of SLO moving images need only be set as a reference frame for registration of all the SLO moving images Dj, thereby performing inter-frame registration.

With the above arrangement, the image processing apparatus 10 can determine an exceptional frame from the SLO moving image D using the image features which have been obtained by the registration unit 145 in registration processing. This enables to calculate a displacement amount with respect to the reference frame more correctly and efficiently, thereby determining an exceptional frame. Furthermore, it is possible to robustly extract a blood vessel or measure the blood cell kinetics even if an eye portion moving image includes an exceptional frame which is inappropriate for measuring blood cell kinetics or the shape of a blood vessel.

Note that contents displayed by a display unit 144 of the image processing apparatus 10 are not limited to those described above. An example of display contents displayed by the display unit 144 will be described with reference to FIGS. 11A, 11B, and 12A to 12C.

FIG. 11A shows an example of a display screen 1100 for the measurement result of an individual SLO moving image. A wide field of view image L, a pasted SLO image N, a SLO moving image I, a blood vessel image V, a time-space image ST generated at a blood flow measurement position, a statistic table T for hemodynamics, a blood flow velocity graph G1, and a phase graph G2 are displayed on the display screen 1100.

An imaging position H of the SLO moving image I is superimposed on the wide field of view image L, thereby enabling to identify the positional relationship between the imaging position and eye tissue A. Furthermore, the currently selected imaging position H of the SLO moving image I is displayed in color different from that for other imaging positions.

The SLO moving image I in the middle of the upper portion of the screen is a moving image having undergone inter-frame registration, on which the flow of a blood cell pt can be observed. A scale R indicating the physical size of the image is displayed in the corner of the SLO moving image I. Operation buttons 1101 (stop, pause, play, frame-by-frame backward playback, and frame-by-frame forward playback buttons from left) and a refresh rate adjustment bar (not shown) are arranged below the SLO moving image I, which are operated to control a moving image playback method. All pixel values in a frame which has been determined as an exceptional frame in the SLO moving image I are displayed as 0 (that is, a black frame), thereby notifying that the frame is an exceptional frame. A bar S which is used to represent the magnitude of pulse data value in a frame being played back by the length of a gray bar is displayed above the SLO moving image I.

Blood capillaries (a white area) extracted from the SLO moving image I is displayed in the blood vessel image V, and set measurement positions (L1, L2, and L3) of a blood cell moving speed are displayed in the blood capillary area. Different colors are respectively assigned to the lines L1, L2 and L3 indicating the measurement positions, and the same color as that of each line is assigned to a velocity value graph corresponding to the measurement position indicated by the line so as to easily identify a corresponding blood flow velocity value on the blood flow velocity graph G1. Based on an instruction input by the operator through an instruction obtaining unit 150, it is possible to modify or delete the measurement positions, or adjust the contrast of the blood vessel image V.

The time-space image ST is a curved cross-sectional image generated by extracting the SLO moving image I having undergone registration at a measurement position on the blood vessel image V, in which the upper left point represents the origin point, the abscissa represents the measurement position, and the ordinate represents a scanning time. When a blood cell passes through the measurement position, a high-luminance linear locus appears on the time-space image. Using the method in steps S730 to S750 in the first embodiment, a blood cell movement locus is detected, and the detected line is displayed in color. It is possible to calculate a blood cell moving speed based on the angle of the locus on the time-space image ST. Furthermore, it is possible to modify or delete the locus according to an instruction input by the operator through the instruction obtaining unit 150, and the value of a corresponding speed graph is also modified or deleted according to the modification or deletion operation.

In order to make it easy to identify the correspondence between the phase of pulse data and the scanning time (the ordinate) on the time-space image, pulse data information B1 is displayed near the time-space image. In this embodiment, the pulse data information B1 is represented by a bar and the vertical direction represents a time. A larger value of the pulse data indicates a higher luminance. Note that the method of displaying the pulse data information is not limited to this, and a pulse data graph with the abscissa representing the magnitude of the pulse data and the ordinate representing the time may be displayed near the time-space image. Furthermore, a bar J indicating a range B3 of an exceptional frame in the time-space image may be displayed. In the exceptional frame range bar J, a non-exceptional frame range B2 is displayed in color different from that of the exceptional frame range B3.

The statistic/index table T for hemodynamics includes the statistics or indices of a blood flow velocity value, which have been measured at the respective measurement positions (L1, L2, and L3). Average (ave)/minimum (min)/maximum (max) values are displayed as the statistics, and a pulsatility index (PI), resistance index (RI), and blood flow rate (Flow) are displayed as the indices. Note that since calculation of the blood flow rate requires a blood vessel diameter, the image feature obtaining unit 1411 sets the center line of the blood vessel by executing thinning processing for the blood vessel area, or the position of the center line of the blood vessel specified by the user is input through the instruction obtaining unit 150, after the blood vessel extraction processing (S720). After setting the center line, the blood vessel diameter is calculated as the length of a high luminance range in a direction perpendicular to the center line, thereby obtaining the blood flow rate. Furthermore, a blood flow velocity may be positive or negative. If, however, the operator wants to evaluate the absolute value of the blood flow velocity irrespective of the blood cell flow direction (forward/reverse), it is preferable to be able to display statistics or indices for the absolute value of the blood flow velocity value by switching a button (not shown).

Figure 11B:
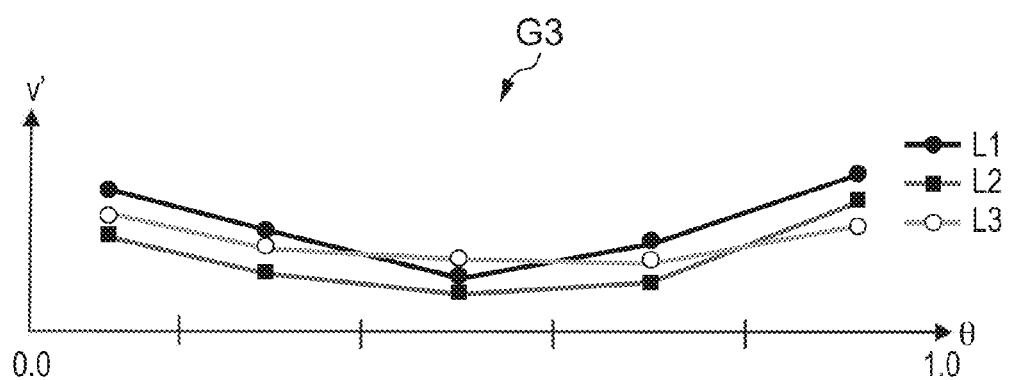
FIG. 11B is a graph showing a blood flow velocity.

The blood flow velocity graph G1 shows a change, with time, in blood cell moving speed value (blood flow velocity) at each measurement position L1, L2, or L3 on the blood vessel image V. By switching on/off of a check box (not shown), display/non-display of a line indicating each speed value is switched for each line (each measurement position). The color of each line is the same as that of a corresponding measurement position, and a point indicating a speed value on the graph is modified or deleted as the detection result of a blood cell movement locus on the time-space image is modified or deleted. Similarly to the statistic/index table T for hemodynamics, it is possible to display a blood flow velocity for the absolute value of the blood flow velocity value by switching a button (not shown). The pulse data graph G2 has the abscissa representing the time and the ordinate representing a pulse data value. The pulse data graph G2 is juxtaposed to the blood flow velocity graph G1 so as to readily identify the relationship between them. On the other hand, FIG. 11B shows a blood flow velocity graph G3 with the abscissa representing a phase (a relative value when the cardiac cycle is 1 (relative cardiac cycle)) and the ordinate representing an average blood flow velocity value within each of small intervals obtained by dividing the phase. By pressing a button (not shown), the pair of the blood flow velocity graph G1 and the pulse data graph G2 where the abscissa represents the time and the blood flow velocity graph G3 where the abscissa represents the relative cardiac cycle are switched for display. Referring to FIG. 11B, each small interval has a length of 0.2, and an average velocity value for each small interval is displayed.

Figure 12A:
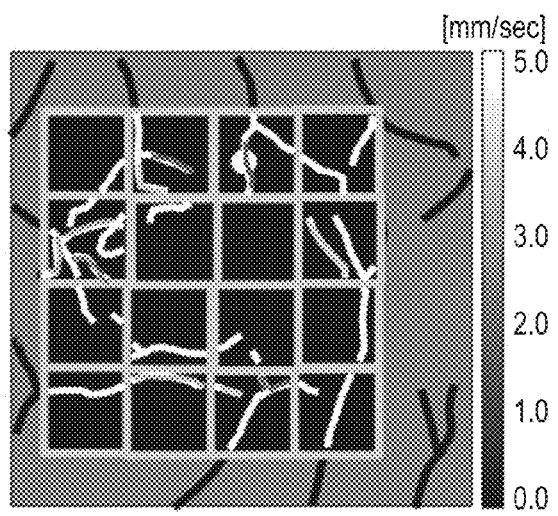
FIGS. 12A to 12C are views each showing an example of a display screen for the measurement result of each of a plurality of SLO moving images obtained by capturing the same eye.
Figure 12B:
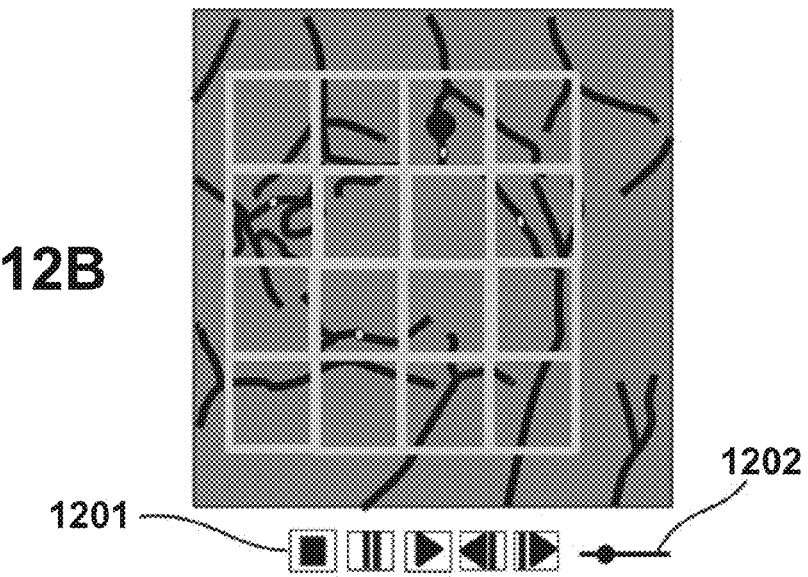
Figure 12C:
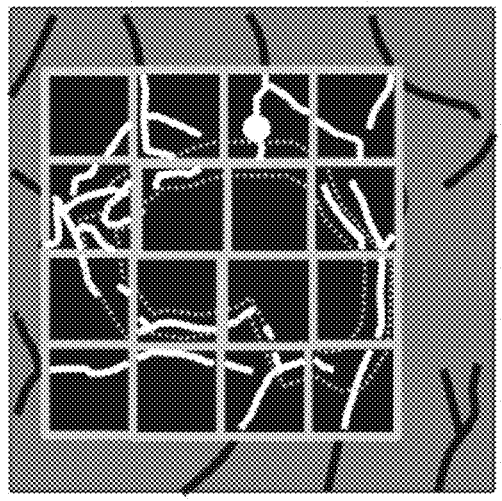

FIGS. 12A to 12C are views each showing an example of a display screen for the measurement result of each of a plurality of SLO moving images obtained by capturing the same eye. FIG. 12A shows a blood flow velocity map on which a blood flow velocity value at a measurement position is superimposed on a pasted blood vessel image in color corresponding to a color table displayed on the right side of the map. With the blood flow velocity map, the user can recognize the ocular circulatory system of an eye to be examined.

In this embodiment, a speed value measured during the telediastolic period on the pulse data is displayed as a blood flow velocity value. Note that the method of displaying the blood flow velocity map is not limited to this, and the statistics (average, minimum, and maximum values) of a blood flow velocity may be displayed. Alternatively, an index (pulsatility index or resistance index) map for hemodynamics or a blood flow rate map may be displayed as a blood flow map. Furthermore, for a blood flow velocity/the statistics of the blood flow velocity/an index for hemodynamics/a blood flow rate, a difference with respect to a normal value range such as a deviation or statistical significance may be displayed as a color map. Although the measurement value of the blood flow velocity is displayed on the blood vessel image in color in this embodiment, the present invention is not limited to the blood vessel image. For example, a SLO moving image, a specific frame of the SLO moving image, or a superimposed image may be used. Color assignment in the color table may be arbitrary. Furthermore, a measurement value may be displayed near a corresponding measurement position.

The measurement value map for the plurality of SLO moving images displayed by the display unit 144 is not limited to that for the ocular circulatory system. As shown in FIG. 12C, for example, the area of an avascular area (an area within an inner closed curve) and a blood vessel density in an area (an area surrounded by two closed curve) near the avascular area may be displayed on the pasted blood vessel image. The blood vessel density is defined as the length of a blood vessel per unit area. Alternatively, the image feature obtaining unit 1411 may set the center line of the blood vessel by executing thinning processing for the blood vessel area, or the position of the center line of the blood vessel specified by the user may be input through the instruction obtaining unit 150, thereby calculating the blood vessel diameter in a direction perpendicular to the center line of the blood vessel to display it.

The measurement value map as shown in FIG. 12A or 12C may be juxtaposed to the pasted SLO moving image (FIG. 12B) so as to readily perform comparison with blood cell kinetics. Operation buttons 1201 (stop, pause, play, frame-by-frame backward playback, and frame-by-frame forward playback buttons from left) and a refresh rate adjustment bar 1202 are arranged below the pasted SLO moving image, which are operated to control a moving image playback method. Alternatively, the images in FIGS. 12A, 12B, and 12C may be switched to be displayed. When displaying the images in FIGS. 12A, 12B, and 12C by switching them or juxtaposing them to each other, a dedicated screen may be individually displayed, or may be displayed in the area (N) for displaying the pasted SLO image in FIG. 11A. If the images in FIGS. 12A, 12B, and 12C are displayed in the area N for displaying the SLO image, it is possible to simultaneously check a detailed blood flow analysis result in the single SLO moving image area and the overview of blood flow analysis results in other SLO moving image areas.

Other Embodiments

In the above-described embodiments, an exceptional frame is determined in an AO-SLO image. It is, however, possible to determine an exceptional frame caused by blinking using an anterior eye monitor attached or attachable to a SLO apparatus 20. The anterior eye monitor captures a planer image of the anterior ocular segment as a moving image. An image processing apparatus 10 continuously monitors the obtained moving image, and detects blinking based on the luminance value or image features of the anterior ocular segment, thereby giving feedback on the detection result to the image processing apparatus 10. An exceptional frame determination unit 141 can determine, as an exceptional frame caused by blinking, an AO-SLO image obtained at the detection timing. Similarly, it is also possible to determine an exceptional frame caused by fixation disparity.

Furthermore, it is possible to determine an exceptional frame caused by an aberration correction error without using an AO-SLO moving image. In an AO-SLO apparatus which measures and corrects aberration in real time, the image processing apparatus 10 continuously monitors the difference between aberration measured by an aberration measuring device and aberration corrected by an aberration correction device. This difference indicates the value of aberration which cannot be corrected by the device. The exceptional frame determination unit 141 can determine whether the difference is larger than a threshold, and then determine, as an exceptional frame, an AO-SLO image obtained when it is determined that the difference is larger than the threshold.

Although the embodiments have been described in detail, the present invention can adopt an embodiment in the form of, for example, a system, apparatus, method, program, or storage medium. More specifically, the present invention may be applied to a system constituted by a plurality of devices, or an apparatus comprising a single device.

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-034539, filed Feb. 20, 2012, and Japanese Patent Application No. 2012-245637 filed Nov. 7, 2012, which are hereby incorporated by reference herein in their entirety.

The invention claimed is:

1. An image processing apparatus comprising:
    a determination unit configured to determine one or more exceptional frames of a plurality of frames forming a moving image captured by an ophthalmic apparatus including an aberration correction device; and
    a processing unit configured to apply image processing of a blood vessel area for a frame, among the plurality of frames, which has not been determined as the one or more exceptional frames,
    wherein said determination unit determines a degree of an exception for each of the one or more exceptional frames, and
    wherein said processing unit executes blood vessel extraction processing using the plurality of frames, and changes a processing parameter to be applied between (a) the one or more exceptional frames and (b) frames other than the one or more exceptional frames, while changing the processing parameter for the one or more exceptional frames according to the degree of the exception.

2. The apparatus according to claim 1, wherein said determination unit determines the one or more exceptional frames among the plurality of frames forming the moving image based on an image feature of each frame.

3. The apparatus according to claim 2, wherein the image feature is at least one of a luminance value, a change amount of a distance between feature points, a signal to noise ratio, and a change amount with respect to a set reference frame.

4. The apparatus according to claim 2, wherein said determination unit determines, as the one or more exceptional frames, a frame which includes no specific part, tissue, cell, or lesion, or which includes not more than a given proportion of a specific part, tissue, cell, or lesion.

5. The apparatus according to claim 1, wherein based on a displacement amount with respect to a reference frame set in a specific one of the plurality of frames obtained several times, said determination unit determines the one or more exceptional frames from the plurality of frames.

6. The apparatus according to claim 1, further comprising a registration unit configured to perform inter-frame registration for the plurality of frames of the moving image,
    wherein said determination unit determines the one or more exceptional frames using an image feature obtained from a single frame for each frame before the inter-frame registration, and determines the one or more exceptional frames using an image feature based on a difference between frames for each frame after the inter-frame registration.

* * * * *